(12) United States Patent
Mukherjee et al.

(10) Patent No.: US 6,569,464 B1
(45) Date of Patent: May 27, 2003

(54) **COELOMIC FLUID EXTRACT FROM *PHERETIMA POSTHUMA* FOR PROVIDING SPERM IMMOTILITY**

(75) Inventors: Mohua Mukherjee, Calcutta (IN); Shampa Biswas, Calcutta (IN); Malabika Datta, Calcutta (IN); Samir Bhattacharya, Calcutta (IN); Ranjan Bhadra, Calcutta (IN); Alok Pal, Calcutta (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 09/822,756

(22) Filed: Mar. 30, 2001

(51) Int. Cl.⁷ .................. A01N 63/00; A01N 65/00; A61K 35/12; C12N 5/00; C12N 5/02
(52) U.S. Cl. ........................ 424/520; 435/325
(58) Field of Search ................ 435/325, 348, 435/FOR 100; 424/93.1, 9.2, 93.7, 520, DIG. 14

(56) References Cited

U.S. PATENT DOCUMENTS 3,741,997 A * 6/1973 Berndt et al. ............... 552/509
3,892,842 A * 7/1975 Zaffaroni .................... 424/432

* cited by examiner

Primary Examiner—David M. Naff
Assistant Examiner—Deborah K. Ware
(74) Attorney, Agent, or Firm—McDonnell Boehnen Hulbert & Berghoff

(57) ABSTRACT

A sperm immotility and anti-fertility agent is provided. The agent comprises coelomic fluid extract which is obtained from an Indian earthworm, *Pheretima posthuma*, belonging to the phylum, Annelida. The agent may further comprise pharmaceutically acceptable additives and can be in the form of a solution, gel, powder, capsules, tablets or cream. The agent is a non-steroid and also can be used externally. Upon further purification a protein can be isolated having a molecular weight of 20 kilodaltons. This protein is anionic and non-toxic and also is without hemolytic activity. Also the protein as well as the extract can provide 100% sperm immotility within 2 minutes. In addition, methods of isolation of an active factor of the coelomic fluid, determination of toxicity and hemolytic activity of the agent as well as preparing a sperm suspension from male rats and mice useful for bio-assay are disclosed.

6 Claims, 3 Drawing Sheets

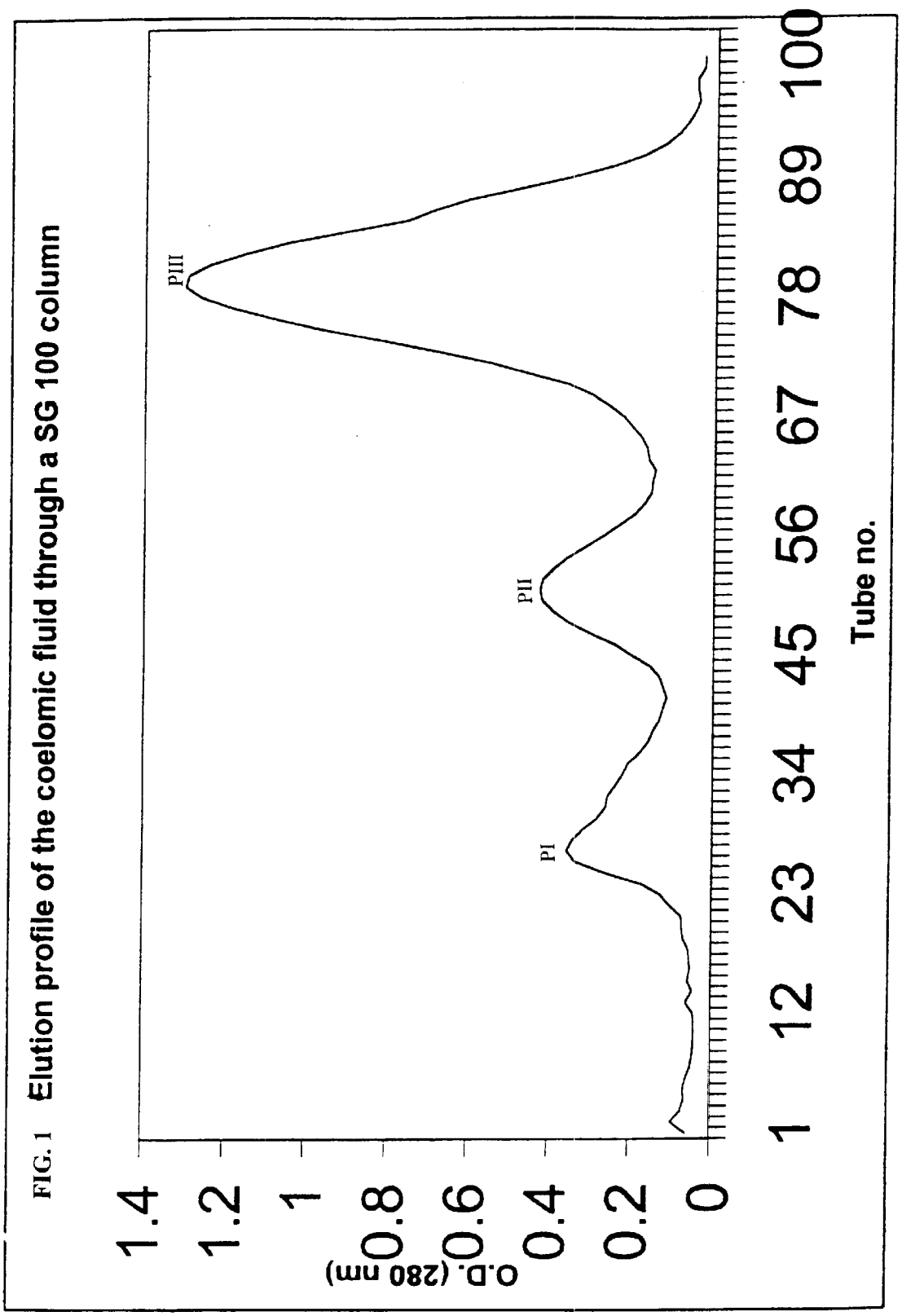
FIG. 1 Elution profile of the coelomic fluid through a SG 100 column

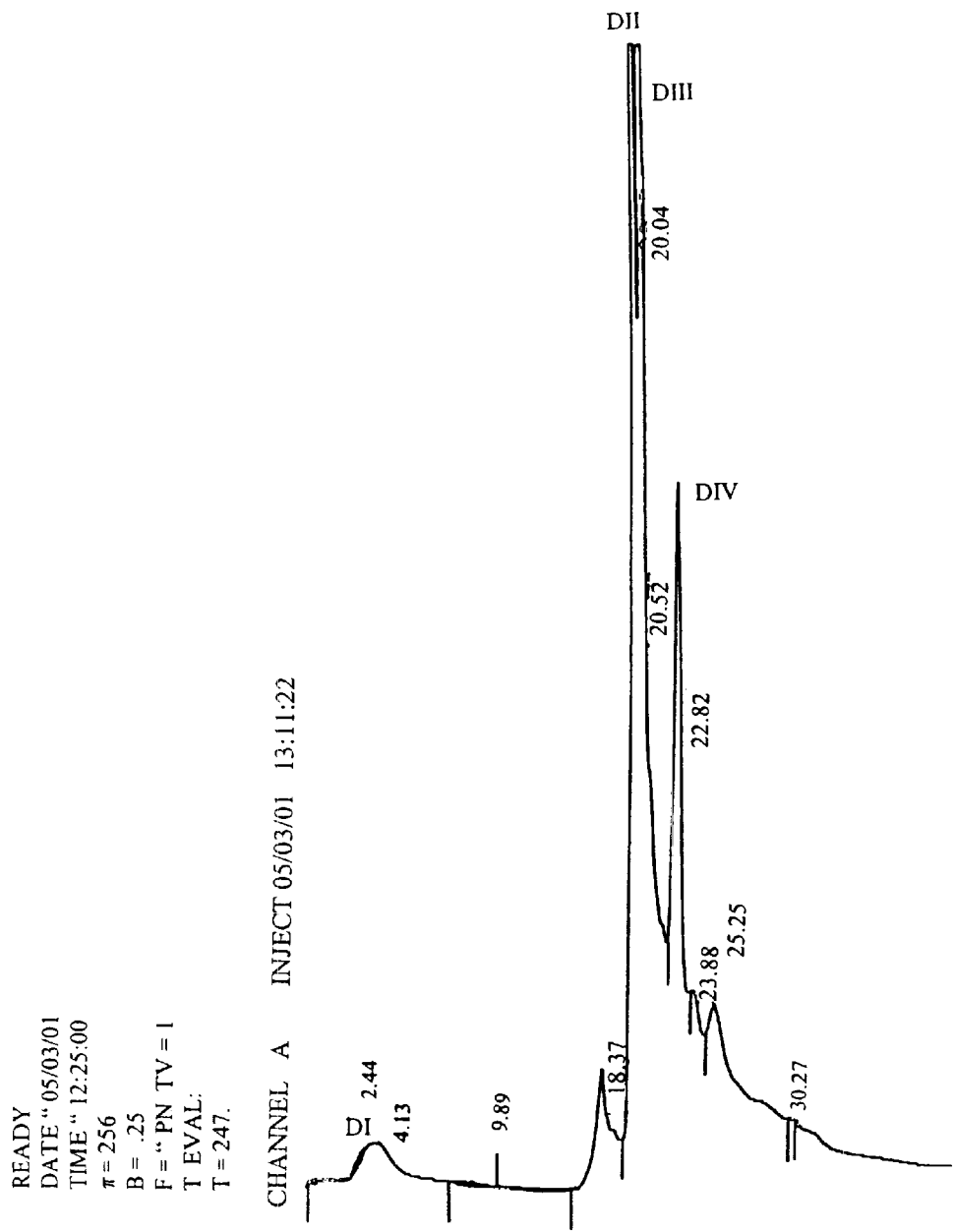

FIG. 3 – SDS – PAGE
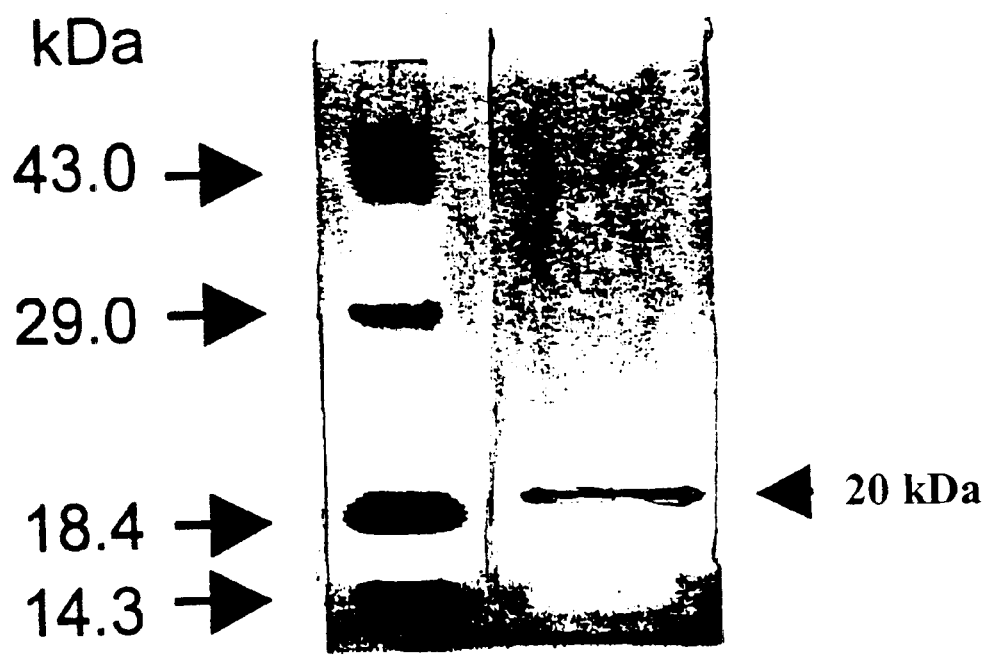

COELOMIC FLUID EXTRACT FROM *PHERETIMA POSTHUMA* FOR PROVIDING SPERM IMMOTILITY

FIELD OF THE INVENTION

The present invention relates to a novel sperm immotility protein isolated from an earthworm, *Pheretima posthuma*, belonging to the phylum, Annelida useful as an anti fertility agent. The invention also provides a method for the isolation of an active factor in the Coelmic Fluid (CF) of commonly available mature specimens of the earthworm, *Pheretima posthuma* belonging to the phylum, Annelida useful as an anti fertility agent.

BACKGROUND OF THE INVENTION

Control of population explosion is a highly significant program related to the progress of any developing countries like India and China. There are some contraceptive devices and agents in the market, which are no doubt helpful in regulating the fertility and therefore population control but most of them pose problems either in relation to the total success or toxic side effects as in the case of the contraceptive pills which contains steroids. Hence, we really need a very successful device or product that will not only assure a total success but also would not produce harmful side effects.

Hence, attempts from various countries are directed to avail such a product and till date a total success has not been achieved. There is an interesting story in Japan. An ex-Emeritus Professor of Tokyo University with a group of investigators started a research program on the availability of a contraceptive agent from the coelomic fluid of *Eisenia foetida*. Addition of a factor from the coelomic fluid of Japanese earthworm, *Eisenia foetida* immediately stopped sperm motility of a number of vertebrates including human beings. The group was very excited and went on purifying the factor, which is a protein and found it to be a monomeric protein of 41 kDa. Later, when they even cloned the gene of this protein they suddenly discovered the high toxicity of this protein (Sekizawa et al., 1996, *Biomed. Res.,* 17(3), 197–203; Sekizawa et al., 1997, *Gene,* 191, 97–102; Yamaji et al., 1998, *J. Biol. Chem.,* 273(9), 5300–5306; Kobayashi et al., 2000, *J. Expl. Zool.,* 286, 538–549). Injection of this protein into the blood immediately killed rats and mice. Addition of this protein into RBC preparation lysed the cells instantaneously. This incident spoiled their objective but they could observe another important aspect of this protein i.e. its specificity to bind sphingomyelin, a lipid invariably occurring in the cell membrane of majority of the vertebrates. It is due to this binding that the cell is lysed. However, they found a highly specific sphingomyelin binding protein, which is an exceptionally important protein as such proteins are still not available. It is named as lysenin and is marketed at high price due to its sphingomyelin binding property. They also published a number of papers on lysenin.

Clearly, their major objective was a failure i.e. its use as an agent for antifertility where commercial value would have been more.

OBJECTS OF THE INVENTION

The main object of this invention is to identify a factor from the Coelomic Fluid (CF) of an earthworm, which causes instant immotility of sperms and can be used as an anti-fertility agent.

Another object of the invention is to project the factor as a totally non-toxic compound as compared to the other contraceptive agents available in the market day, which manifest severe side effects.

SUMMARY OF THE INVENTION

The applicants initiated work with an Indian earthworm *Pheretima posthuma,* extracted the coelomic fluid and tested them on sperm motility and found that it also immediately stopped sperm movement, as effectively as lysenin. But there is a conspicuous difference. The extracted material from Indian earthworm did not produce any mortality of rats, mice or rabbits. A thorough examination on this toxicity showed no harmful effect on liver function or the function of other tissues. Moreover, its addition to RBC preparation did not produce any lysis of the cells as has been observed with lysenin. Hence, the extracted material has the property for causing instantaneous immotility of sperm without adverse side effects. This is a genuine advantage and could be profitably utilized for fertility control. This factor is also a protein. The applicants also have purified it through molecular exclusion chromatography (SG-100) followed by HPLC anionic chromatography. Hence, it is a new product from an Indian earthworm source and requires protection.

BRIEF DESCRIPTION OF DRAWINGS

FIG. 1: Elution profile of the Coelomic Fluid through a SG 100 gel filtration column, three peaks, PI, PII and PIII were obtained. Proteins from each peak were tested for their activity on sperm immotiliy.

FIG. 2. Elution profile of P III (the active peak of gel chromatography) through a HPLC DEAE column. One small unbound peak (D I) and three bound peaks (DII, DIII and DIV) were obtained, proteins from each peak were tested for their activity on sperm immotiliy.

FIG. 3. SDS-PAGE of the active fraction of the ion exchange chromatographic step on a 12% separating gel and 3.5% stacking gel. About 3 µg of the protein was dissolved in 20 µl of the sample buffer containing 0.01 M Tris, 10% SDS, 5% β-mercaptoethanol and 0.1% bromophenol blue, (pH 6.8). It was heated for 5 min at 100° C. and loaded on the gel and run at 50V. 7 µl of prestained marker (GIBCO-BRL) was used for determination of the molecular weight. A single monomeric protein of 20 kDa was obtained (FIG. 3).

BRIEF DESCRIPTION OF TABLES

Table 1: Data of the addition of each protein peak to sperm suspension to check their immotility. 15 µg of each protein peak was added to the sperm suspension and their effect in causing immobility was monitored at 30 sec, 2 min, 5 min and 10 min. Only P III caused 100% immotility while PI and P II had no effect.

Table 2: Data of the addition of each protein peak to sperm suspension to check their immotility. 5 µg of each protein peak was added to the sperm suspension and the effect in causing immotility was monitored at 30 sec, 2 min, 5 min and 10 min. 100% immotility of the sperms was caused by protein of the 1$^{st}$ bound peak indicating the presence of the active factor in this fraction.

DETAILED DESCRIPTION OF THE INVENTION

Accordingly, the present invention provides a novel sperm immotility protein isolated from an earthworm, *Pheretima posthuma* having the following characteristics:

(a) anionic protein, (b) molecular weight of 20 kDa, (c) non-toxic and without any hemolytic activity, and (d) causes 100% sperm immotility within 2 min.

In an embodiment of the present invention, the protein when a dose ranging from 10–15 mg/Kg body weight is administered to rats and mice for a month does not have any adverse effect.

In another embodiment of the invention, the protein is capable of being used for internal and external application on a mammalian body including humans.

In still another embodiment of the invention, the sperm immotility agent which is also useful as an anti fertility agent, comprising Coelomic Fluid extract obtained from an earthworm, *Pheretima posthuma,* belonging to the phylum, Annelida.

In still another embodiment, the novel sperm immotility agent further comprising conventional pharmaceutically acceptable additives.

In yet another embodiment of the invention, the novel sperm immotility agent is in the form of solution, gel, powder, capsules, tablets and cream.

In yet another embodiment of the invention, the novel sperm immotility agent is non-toxic and does not show any hemolytic activity when injected in mammals.

In yet another embodiment of the invention, the novel sperm immotility agent shows 100% sperm immotility within two minutes.

In yet another embodiment of the invention, the novel sperm immotility agent is a non-steroid and can be used externally.

One more embodiment of the invention relates to a method for the isolation of an active factor in the CF (Coelomic Fluid) of commonly available mature specimens of the earthworm, *Pheretima posthuma,* wherein the said method comprising the steps of:

a. providing coelomic fluid (CF) from the commonly available mature specimens of the earthworm, *Pheretima posthuma* and subjecting the CF to ultra-sonication followed by centrifugation, b. obtaining the supernatant as the crude extract of CF, c. subjecting the crude extract of CF to gel filtration chromatography, d. monitoring the protein fractions at 280 nm, e. obtaining three protein peaks and assaying the activity in each peak, f. collecting the active peak III, lyophilising, dialysing and subjecting it to HPLC on a DEAE column for further purification, g. eluting the unbound and bound proteins.

h. studying the absorbance of each protein peak at 280 nm, i. pooling, lyophilizing and dialysing each peak and checking their activity on sperm mobility, and j. identifying the 1st bound peak showing the sperm immotility effect and subjecting it to SDS-PAGE for the determination of its purity and molecular weight.

In another embodiment of the invention, said CF is subjected to immortality test by injecting it to rats and mice at a dose ranging from 10–15 mg/kg body weight showing no mortality even after one month of such injections.

In still another embodiment of the invention relates to a method wherein, conducting tests for hemolysis using rat RBCs by adding a dose of 10 $\mu$l of the crude extract to 250 $\mu$l of RBC preparation showing intact RBCs even after 30 min of incubation indicating the protein without any hemolytic activity.

In yet another embodiment provides a method of preparing a sperm suspension from male rats and mice, to be used in bioassay, said method comprising the steps of:

a. collecting sperms from fertile male rats and mice and diluted in BWW medium, equilibrated under oil coverage at 37° C. in the presence of 5% $CO_2$ in air in a $CO_2$ incubator.

b. incubating the sperm suspension again to allow the spermatozoa to swim up, c. collecting highly motile sperm suspension having at least 70% forward motility, and d. centrifuging the sperm suspension for about 5–10 min and diluting the pelleted sperms to attain the required concentration of 40–50 $\mu$l ($2.0 \times 10^5$–$2.5 \times 10^5$ sperms).

In yet another embodiment, the anti fertility compound capable of being used externally or internally in mammals obtained from an earthworm, *Pheretima posthuma,* belonging to the phylum, Annelida.

I Bioassay of the active principle:

(a) Collection of sperm and preparation of sperm suspension.

Sperms for the assay were collected from the cauda of fertile male rats and mice and diluted in BWW medium (94 mM NaCl, 4.7 mM KCl, 1.7 mM $CaCl_2$, 1.2 mM $KH_2PO_4$, 1.2 mM $MgSO_4.7H2O$, 25 mM $NaHCO_3$, 0.5 mM Na-pyruvate, 19 mM Na-lactate, 5 mM glucose, 0.4% BSA, 0.1% antibiotic solution, pH 7.2) which was equilibrated under oil coverage at 37° C. in the presence of 5% $CO_2$ in air in a $CO_2$ incubator. The sperm suspension was again incubated to allow the spematozoa to swim up. After an hour, swim up sperms were collected from the top of the sperm suspension. The concentration of the swim up sperms was determined in a Maclar's chamber. The nature and motility of the sperms were also checked. Highly motile sperm suspension having at least 70% forward motility was considered for the experiment. The swim up sperms was collected from the top of the sperm suspension; centrifuged at 1000 rpm for five minutes and the pelleted sperms were diluted to attain the required concentration. 50 $\mu$l ($2.5 \times 10^5$ sperms) of the sperm suspension was placed in 35 mm disposable petri dishes and covered with mineral oil (Sigma) which was pre-equilibrated in the $CO_2$ incubator in 5% $CO_2$ in air overnight.

(b) Effect of the various protein fractions on sperm motility.

All the fractions to be tested for sperm immotility were diluted in phosphate buffered saline (PBS). 50 $\mu$l test materials was added to the sperm suspension drop: for control study equal volume of PBS was added instead of test solution. Nature of sperm motility was observed under the microscope at an interval of 30 sec, 2 min, 5 min and 10 min after addition of test materials. During this phase the culture dishes were maintained in a $CO_2$ incubator. After the final observation pH of all test drops were recorded to confirm any deviation of pH of the test suspension.

II. Extraction and Purification of the active principle:

Mature specimens of earthworms were pricked with a sterile needle. Approximately 100 such worms were taken in a beaker and subjected to ultrasonication for 45 min. 15 ml of the coelomic fluid (CF) was obtained by this method. This was centrifuged at 10,000 rpm for 20 min. The supernatant was stored at −20° C. and used as the crude extract of CF and also for further purification of the active principle.

(a) Molecular Exclusion chromatography:

The CF was subjected to gel filtration chromatography on a Sephadex G 100 column (1.5×80 cm) pre-equilibrated with 0.05 M PBS (pH 7.2). 0.5 ml of CF was loaded onto the column. The column was eluted with the same buffer at a flow rate of 20 ml/h and 2.0 ml fractions were collected. The absorbance of the fractions was monitored at 280 nm. Three protein peaks were obtained (FIG. 1) and the activity was assayed in each peak (Table 1). Fractions of the active peak (P III) were pooled, lyophilized and dialysed (against 0.005 M phosphate buffer for 24 h at 4° C. with two changes of buffer) and subjected to ion exchange chromatography on a HPLC DEAE column.

(b) Ion exchange chromatography:

The active fraction of the molecular exchange chromatographic step (P III) was further purified on a HPLC DEAE column (7.5×750 mm) equilibrated with Buffer A (0.005 M phosphate buffer (pH 7.0)). Unbound proteins were eluted by washing the column with the same buffer at a flow rate of 0.8 ml/min. Bound proteins were eluted with Buffer B (Buffer A plus 2.0 M NaCl). The absorbance of each protein fraction was monitored at 280 nm. A small unbound peak and three bound peaks were obtained (FIG. 2). Each peak was separately pooled, lyophilized and dialysed (against 0.005 M phosphate buffer for 24 h at 4° C. with two changes of buffer) and checked for their activity on sperm motility (Table 2). The $1^{st}$ bound peak showed the sperm immotility effect and it was subjected to SDS-PAGE.

(c) SDS-PAGE:

The active peak of the ion exchange chromatography step was subjected to SDS-PAGE on a 12% separating gel and 3.5% stacking gel. About 3 μg of the protein was dissolved in 20 μl of the sample buffer containing 0.01 M Tris, 10% SDS, 5% β-mercaptoethanol and 0.1% bromophenol blue, (pH 6.8). It was heated for 5 min at 100° C. and loaded on the gel and run at 50V. 7 μl of prestained marker (GIBCO-BRL) was used for determination of the molecular weight. A single monomeric protein of 20 kDa was obtained (FIG. 3).

III. Toxicity tests:

(a) Mortality test:

To check whether the coelomic fluid has any toxic effect or not, the crude extract was injected (i.v and i.p) to rats and mice (five each) at a dose of 15 mg/kg body weight. Control animals were injected an equal volume of 0.9% saline. There was no mortality of any animal even after one month of injection.

(b) Test for Hemolysis:

Rat RBCs were prepared immediately after collecting blood in a heparinised tube. The blood was diluted 3 times with isotonic saline and centrifuged at 1000 rpm for 5 minutes. The pelleted RBCs were washed five times with saline and diluted to about $2 \times 10^5$ cells/ml. 10 μl of the crude extract (0.19 mg) was added to 50 μl of the RBC preparation and observed under the microscope. All the RBCs were intact even after 30 min of incubation indicating that this protein is without any hemolytic activity.

Having done all the in vitro and in vivo tests, the applicants are definitely in a position to claim the identification of a factor in the coelomic fluid of *Pheretima posthuma* which has a strong effect in causing immotility of sperms and at the same time is totally non-toxic. This 20 kDa protein is a strong sperm immotility agent and found to have similar concentration effect in mouse, rat and human being when number of sperms in the plate remains constant. Thus, it has a strong potential to be used as an anti-fertility agent in humans which has no side-effects as is seen in most of the steroid containing contraceptive agents available in the market today. This would be the first non-steroidal and external agent (to be inserted in the vagina) in the market.

The preliminary experiment clearly showed its promise as an externally applied agent.

TABLE 1

Sperm Immotility effect of different peaks of SG 100 elution

| Sl. No | 30 sec | 2 min | 5 min | 10 min |
|---|---|---|---|---|
| PI | No immotility | No immotility | No immotility | No immotility |
| PII | No immotility | No immotility | No immotility | No immotility |
| PIII | 80% immotile | 100% immotile | — | — |

50 μl ($2.5 \times 10^5$ sperms) was taken for each test and 15 μg protein of each peak was added.
Results are obtained from data of five observations.

TABLE 2

Sperm Immotility effect of different peaks of HPLC DEAE ion exchange chromatography.

| Sl. No | 30 sec | 2 min | 5 min | 10 min |
|---|---|---|---|---|
| DI | No immotility | No immotility | No immotility | No immotility |
| DII | 70% immotile | 100% immotile | — | — |
| DIII | 10% immotile | 15% immotile | 15% immotile | 15% immotile |
| DIV | No immotility | No immotility | No immotility | No immotility |

50 μl ($2.5 \times 10^5$ sperms) was taken for each test and 5 μg protein of each peak was added.
Results are obtained from data of five observations.

What is claimed is:

1. A sperm immotility and anti-fertility agent, comprising coelomic fluid extract obtained from an earthworm, *Pheretima posthuma*, belonging to the phylum, Annelida.

2. A sperm immotility and anti-fertility agent as claimed in claim 1 further comprising pharmaceutically acceptable additives.

3. A sperm immotility and anti-fertility agent as claimed in claim 2 which is in the form of a gel, a powder, a capsule, a solution, a tablet or a cream.

4. A sperm immotility and anti-fertility agent as claimed in claim 1 which is non-toxic and does not show any hemolytic activity when injected in mammals.

5. A sperm immotility and anti-fertility agent as claimed in claim 1 or 2 which shows 100% sperm immotility within two minutes.

6. A sperm immotility and anti-fertility agent as claimed in claim 1 which is a non-steroid and can be used externally.

* * * * *